United States Patent [19]

Lehmann et al.

[11] Patent Number: 4,644,031
[45] Date of Patent: Feb. 17, 1987

[54] COATING FOR PHARMACEUTICAL DOSAGE FORMS

[75] Inventors: Klaus Lehmann, Rossdorf; Dieter Dreher, Darmstadt; Harry Goetz, Alsbach-Haehnlein, all of Fed. Rep. of Germany

[73] Assignee: Röhm GmbH, Darmstadt, Fed. Rep. of Germany

[21] Appl. No.: 697,288

[22] Filed: Feb. 1, 1985

[30] Foreign Application Priority Data

Feb. 15, 1984 [DE] Fed. Rep. of Germany ....... 3405378

[51] Int. Cl.$^4$ .................. A61K 9/32; A01N 25/10; C08L 33/00
[52] U.S. Cl. ............................. 524/501; 427/3; 424/33; 524/522; 524/523
[58] Field of Search ............... 427/3; 424/33; 524/501, 524/522, 523

[56] References Cited

U.S. PATENT DOCUMENTS

| 3,538,214 | 11/1970 | Polli et al. | 424/33 |
| 3,935,326 | 1/1976 | Groppenbacher et al. | 427/3 |
| 4,017,647 | 4/1977 | Ohno et al. | 424/33 |
| 4,350,782 | 9/1982 | Küchler et al. | 524/501 |
| 4,415,547 | 11/1983 | Yu et al. | 424/33 |
| 4,433,076 | 2/1984 | Bauer et al. | 523/342 |
| 4,442,248 | 4/1984 | Kanda et al. | 524/501 |
| 4,452,862 | 6/1984 | Markert et al. | 524/385 |
| 4,504,609 | 3/1985 | Kuwajima et al. | 524/501 |
| 4,510,275 | 4/1985 | Ihikura et al. | 524/522 |
| 4,520,172 | 5/1985 | Lehmann et al. | 525/369 |

FOREIGN PATENT DOCUMENTS

| 52075 | 5/1982 | European Pat. Off. . | |
| 1467855 | 2/1968 | Fed. Rep. of Germany | 424/33 |
| 1617351 | 1/1972 | Fed. Rep. of Germany . | |
| 2135073 | 12/1973 | Fed. Rep. of Germany . | |
| 3127237 | 1/1983 | Fed. Rep. of Germany . | |
| 3134222 | 3/1983 | Fed. Rep. of Germany . | |
| 1393374 | 5/1975 | United Kingdom . | |

Primary Examiner—Ronald W. Griffin
Attorney, Agent, or Firm—Curtis, Morris & Safford

[57] ABSTRACT

Coated pharmaceutical dosage forms which are resistant to gastric juice and release their active ingredient rapidly at a predetermined pH value in the range from pH 5 to pH 8 are obtained in accordance with the invention by coating pharmaceutical dosage forms with an aqueous dispersion containing dispersed latex particles of a first polymer which contains carboxyl groups and is water soluble between pH 5 and pH 8 and of a second water insoluble film forming polymer, in a weight ratio between 60:40 and 5:95.

12 Claims, 1 Drawing Figure

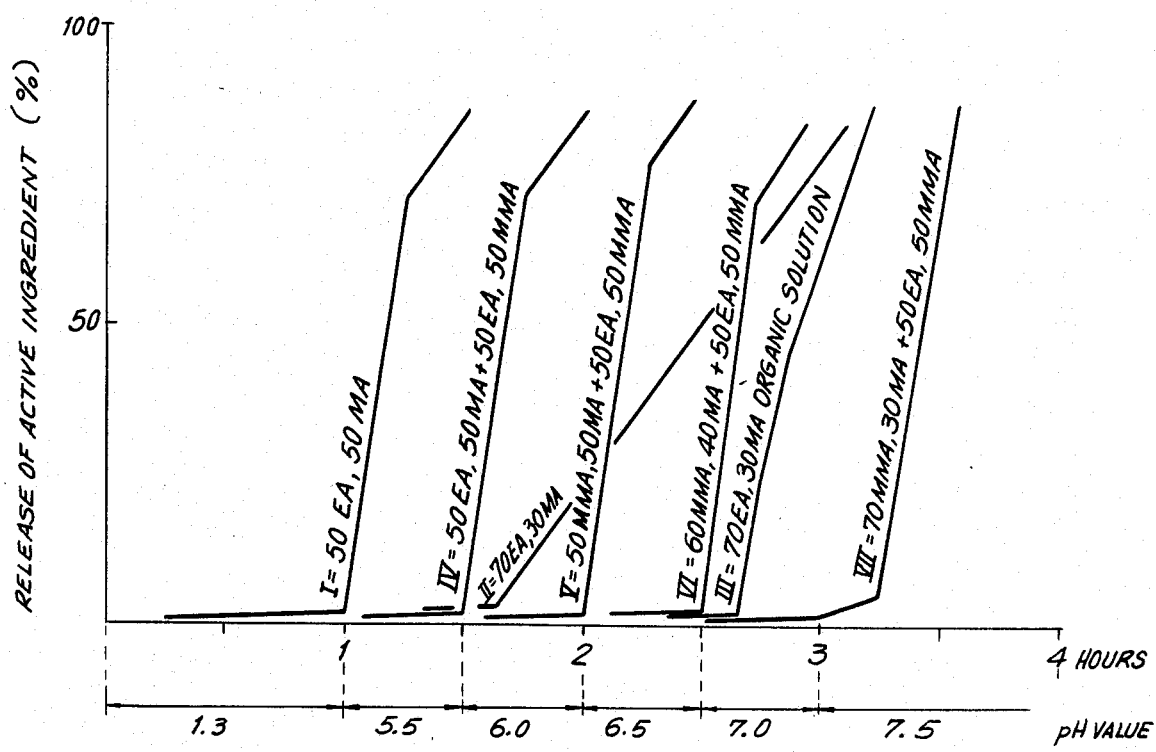

COATING FOR PHARMACEUTICAL DOSAGE FORMS

The present invention relates to a an aqueous dispersion of a synthetic resin having carboxyl groups and of a film forming synthetic resin, said dispersion being adaptable to use as a coating composition for pharmaceutical dosage forms and to pharmaceutical dosage forms coated therewith.

Coating compositions for medicinal tablets containing a water soluble, film forming synthetic resin in the form of an aqueous dispersion and a water soluble or alkali soluble substance are known from German patent publication No. 16 17 351. For coatings which are to be resistant to gastric juice, an alkali soluble substance is used concurrently therewith, which substance is dissolved out of the tablet coating in an alkaline environment and leaves pores through which the active ingredient can then diffuse. Fatty acids, for example, are proposed as alkali soluble substances. The release of active ingredient begins when the tablet enters an aqueous medium having a pH value at which the alkali soluble substance dissolves.

From the same publication it is further known to incorporate into the coating macromolecular water soluble substances, such as polyethylene glycols, which are soluble regardless of the pH value of the medium. The use of alkali soluble macromolecular substances had not been known up to that time; however, it was to be expected that, like low molecular weight alkali soluble substances, they would render the coating diffusion permeable at a pH value at which they are soluble.

The combination of a dispersed acrylate polymer with a water insoluble cellulose ether is known from European patent publication No. 52 075. It results in coatings for pharmaceutical dosage forms which produce a delayed release of the active ingredient.

According to German patent publication No. 31 27 237, an aqueous dispersion of a coating composition resistant to gastric juice is combined with polyethylene glycol and polyvinyl pyrrolidone to produce dosage form coatings which rapidly decompose in intestinal juice.

Thiele and Pflegel reported in "Pharmazie", 1981, 858–859, and 1983, 43–45, on tablet coatings of aqueous dispersions containing from 98 to 99 weight percent of a hydrophobic acrylate/methacrylate polymer incorporating a small number of carboxyl groups and from 1 to 2 weight percent of a hydrophilic copolymer of acrylic or methacrylic acid and acrylate or methacrylate alkyl esters, both percentages being based on the total polymer content. While the addition of the last-mentioned polymeric material enhances the diffusion permeability, it does not result in rapid release of the active ingredient in the alkaline range. With additions of more than 2 weight percent of the hydrophilic polymer, the coating was found to be unstable. A dependence of the permeability on the pH value was not observed. The release of the active ingredient takes place solely by diffusion through the nonporous membrane, largely independently of pH.

Dispersions of polymers which contain from 10 to 55 weight percent of monomeric units carrying carboxyl groups are known for coating dosage forms from German patent publication No. 21 35 073. These give coatings on pharmaceutical dosage forms which dissolve even in the weakly alkaline medium of the upper portions of the intestine, rapidly with a high content of carboxyl groups, more slowly with a low content of carboxyl groups.

There has been a need for supplementing the range of pharmaceutical dosage form coatings in the form of aqueous dispersions with compositions which are film forming at moderately high temperature and which give coatings that are resistant to gastric juice and which release the active ingredient only, but rapidly, in the more alkaline intestinal juice.

Coating compositions are available, dissolved in organic solvents, which result in fast or slow delivery of the active ingredient at any desired pH value in the physiological range. The release characteristics can be controlled over a wide range through the content of carboxyl groups of the polymer. However, this principle cannot be translated to aqueous coating dispersions. Rapid release of the active ingredient is obtained at pH 5.5 with a dispersion of a copolymer of equal parts of ethyl acrylate and methacrylic acid. However, when the acid content is reduced to 30 weight percent, the active ingredient is released much more slowly, although at the same pH value. A shifting of the fast release to a higher pH range also could not be obtained by using a harder polymer formulation, such as one involving partial replacement of the acrylate component with methacrylate. This would merely result in loss of film forming capacity.

Surprisingly, it has now been found that the release range of coatings resistant to gastric juice can be shifted to higher pH values if the pharmaceutical dosage forms are coated with an aqueous coating dispersion which contains, as a coating composition or binder, dispersed latex particles of (A) a polymer containing carboxyl groups which is water soluble between pH 5 and pH 8, and (B) a water insoluble film forming polymer, the ratio of the total weights of the latex particles (A) and (B) being between 60:40 and 5:95.

The release characteristics of the coatings produced in accordance with the invention as compared to other coatings are readily apparent from the accompanying Figure. The latter illustrates the release of the active ingredient coated with different coatings I to VII and which are exposed to a medium the pH value of which is increased stepwise at regular time intervals. This simulates passage through the intestinal tract.

In the tabulation which follows, the following abbreviations are used for the constituents of the copolymers:
EA=Ethyl acrylate
MMA=Methyl methacrylate
MA=Methacrylic acid
The percentages given are weight percent.

The following emulsion polymers were investigated and, unless otherwise stated, were used as a dispersion or mixture of dispersions for film formation (parts and percentages are by weight):
I—50% EA, 50% MA
II—70% EA, 30% MA
III—70% EA, 30% MA; film formation from organic solution
IV—3 parts 50% EA, 50% MA and 7 parts 50% EA, 50% MMA
V—3 parts 50% MMA, 50% MA and 7 parts 50% EA, 50% MMA
VI—3 parts 60% MMA, 40% MA and 7 parts 50% EA, 50% MMA VII—3 parts 70% MMA, 30% MA and 7 parts 50% EA, 50% MMA What is desired is as steep a slope of the release curve as possible from a value as close as possible to the zero line to a value as high as possible. The requirement for resistance to gastric juice may be regarded as satisfied when release of the active ingredient at pH values below pH 4 remains less than 5 percent of the enclosed amount of active ingredient for one hour. As is apparent from the graph in the FIGURE, this behavior is obtained with the coating compositions of the invention at all pH values above pH 5.5, found in the intestinal tract.

Release can be made to occur at any desired pH value by variation of that component of the coating composition which contains the carboxyl groups, whereas in obtaining the data for the FIGURE the film forming component remained unchanged with respect to its nature and amount. It has been found that film formation is not impaired by component (A), which becomes progressively harder from IV to VII. Component (B) can therefore be selected solely on the basis of the requirements of the film forming process.

Remarkably, the release characteristics of the inventive coatings differ considerably from the findings obtained by Thiele and Pflegel on membranes made from 98 to 99 percent of hydrophobic polymers and from 1 to 2 percent of hydrophilic polymers containing carboxyl groups which had been produced from dispersions. While these membranes remained free of pores, examination of the coatings of the invention under an electron microscope has shown that, starting at a certain pH value, the polymer component (A) containing carboxyl groups is dissolved out of the coating with formation of pores. As a result, the rate of release suddenly increases. This behavior was quite unexpected, especially since Thiele and Pflegel had observed no pH dependence of the release characteristics.

Aqueous dispersions of the coating composition are suitable for the manufacture of pharmaceutical dosage forms which are to pass through the stomach unaltered and are to release their active ingredient quickly in a narrowly limited portion of the intestine characterized by its pH value.

The polymer containing carboxyl groups is present in the form of latex particles dispersed in an aqueous phase. The preparation of such latices is described in German patent publication Nos. 21 35 073 and 31 34 222, for example. However, the dispersion of this polymer need not itself be film forming. Hardening monomers such as lower methacrylate esters may therefore form a higher proportion of the polymer than if the dispersion were used alone as coating composition.

The polymer containing carboxyl groups must be water soluble at least in a portion of the pH range between pH 5 and pH 8 but may be water insoluble in the lower portion of that range. To be dispersible in water, it must be water insoluble at least below pH 5. Above pH 8, it will usually be water soluble; however, this property is immaterial for the purposes of the invention. The aqueous dispersion of the latex particles (A) and (B) has in all cases a pH value at which the polymer containing carboxyl groups is not dissolved. (Polymers, unlike other solutes, do not have saturation concentrations. They are either water soluble or water insoluble. If soluble, one can prepare, for example, a 1 percent solution of the polymer).

As a rule, the polymer is produced by free radical emulsion polymerization of vinyl or vinylidene monomers in an aqueous phase. A portion, preferably from 10 to 70 weight percent, and more particularly from 25 to 55 weight percent, of the monomers contains at least one carboxyl group. Preferred vinyl and vinylidene monomers of this type are acrylic acid and methacrylic acid. However, maleic, fumaric, crotonic and itaconic acid are also usable. The remaining portion of the vinyl monomers is free of carboxyl groups and may consist of esters of the carboxylic acids named, and particularly of alkyl esters having from 1 to 8 carbon atoms in the alkyl radical, acrylonitrile or methacrylonitrile, styrene, alpha-methylstyrene, vinyltoluene, vinyl chloride or vinyl esters of fatty acids, for example vinyl acetate. Hydrophilizing neutral comonomers such as acrylamide, methacrylamide or vinylpyrrolidone, or hydroxyalkyl esters of acrylic acid or of methacrylic acid, may go into the composition of the emulsion polymers in limited amounts. They will produce some diffusion permeability of the coating even at low pH values, which is desirable only in special cases.

The amount of the monomers containing carboxyl groups should in each case be such that the polymer is water soluble in the range from pH 5 to pH 8 and that the active ingredient is released at the desired pH value. When the polymer (A) is investigated by itself, it is found that its rate of dissolution is dependent on the carboxyl group content. Hydrophilic comonomers will increase the dissolution rate, while hydrophobic comonomers will decrease it. For the purposes of the invention, water soluble polymers are polymers which, in the form of films having a thickness ranging from 10 to 20 microns, dissolve in artificial intestinal juice of pH 7.5 within not more than 60 minutes with moderate agitation. In the inventive coatings, delayed water solubility has the effect of shifting the point of release to higher pH values.

The rate of dissolution depends also on the molecular weight. The weight average molecular weight generally should not be over 500,000 and preferably ranges from 50,000 to 300,000.

Preferred polymers containing carboxyl groups comprise (A) 10 to 70, preferably 25 to 55, percent by weight of acrylic acid or methacrylic acid, (B) 90–30, preferably 75 to 25, percent by weight of an unsaturated ester monomer, and (C) up to 20 percent by weight of other unsaturated monomers copolymerizable with monomers (A) and (B), with monomers (A) and (B) together being at least 80 percent by weight of the total monomers. The unsaturated ester monomers include the alkyl esters of unsaturated carboxylic acids, particularly those esters of alkanols having 1 to 8 carbon atoms and vinyl esters of saturated fatty acids, such as vinyl acetate or propionate. The unsaturated ester monomers preferably contain a total of 4 to 12 carbon atoms.

An especially preferred group of copolymers comprise (A) 10 to 70, preferably 25 to 55, percent by weight of acrylic acid or methacrylic acid and (B) 90 to 30, preferably 75 to 45, percent by weight of a $C_1$–$C_8$-alkyl ester, preferably a $C_1$–$C_4$-ester, of acrylic acid or of methacrylic acid.

The film forming polymer is also present in the form of latex particles dispersed in an aqueous phase and preferably is also produced by free radical emulsion polymerization of suitable vinyl or vinylidene monomers. A large number of film-forming aqueous polymer dispersions is on the market, and their preparation is generally known from numerous publications.

Emulsion polymers are termed "film forming" when, under the usual conditions of application of aqueous pharmaceutical dosage form coating dispersions, they result in a continuous film which firmly adheres to the coated core. As a rule, such film formation takes place even at room temperature; however, a higher drying temperature may be used. The film forming polymer is usually selected so that in the form of an aqueous latex it has a minimum film forming temperature in conformity with DIN 53787 of not over 60° C., and preferably not over 40° C. This condition is usually satisfied when the dynamic glass-transition temperature (the $T_{\lambda max}$ value in conformity with DIN 53445) is not over 80° C., and preferably not over 60° C.

The emulsion polymers may be composed of the same vinyl monomers as the polymers containing carboxyl groups. However, the proportion of comonomers containing carboxyl groups should be considerably smaller, if not zero. Hydrophilic comonomers, too, should go into the composition of the polymer only in so limited an amount that the polymer is not water soluble in the physiological pH range of the gastrointestinal tract i.e. from pH 1 to pH 8. If the polymer is water soluble only above pH 8, it is still usable.

For the polymer to have film forming capacity, its composition must include a sufficient proportion of "soft" comonomers. These are those vinyl monomers the homopolymers of which have a dynamic glass transition temperature, $T_{\lambda max}$, below 10° C. Among these are, in the first place, the alkyl esters of acrylic acid. As a rule, they should represent from 40 to 80 weight percent of the polymer. However, their proportion should not be so high that the dynamic glass transition temperature is below 0° C., as otherwise the coatings made from them will be too soft or even tacky. Commercial pharmaceutical dosage form coating dispersions for the production of insoluble coating dispersions for diffusion tablets meet these requirements and are well suited for the purposes of the invention.

The balance of the film forming polymers comprises "hard" vinyl monomers, i.e. those forming homopolymers having a dynamic glass transition temperature above 10° C. These comonomers are as a rule present in an amount from 20 to 60 percent, of which up to 5 percent may be unsaturated carboxylic acids. Preferred copolymers comprise from 40 to 80 percent by weight of those alkyl esters of acrylic acid or of methacrylic acid which form a homopolymer having a $T_{\lambda max}$ less than 10° C., particularly acrylates of $C_1$-$C_8$-alkanols; 60 to 20 percent by weight of methacrylate esters forming homopolymers with a $T_{\lambda max}$ greater than 10° C.; and 0 to 5 percent by weight of acrylic acid or methacrylic acids.

The coating composition is advantageously prepared by mixing the latices of the types (A) and (B) in a weight ratio of the two polymer types between 60:40 and 5:95, and preferably between 50:50 and 30:70. Of course, the dispersions to be mixed must be compatible with each other. For example, they must not contain oppositely charged emulsifiers if this would result in coagulation.

The minimum film forming temperature of the coating composition is affected by the mixing ratio. It should be between the minimum film forming temperatures of the starting latices of the polymers (A) and (B). If it is undesirably high, it can be reduced by the addition of film forming aids which either remain in the film as plasticizers or evaporate as volatile solvents during drying. Examples of such film forming aids are ethylene glycol or propylene glycol, glycerine, esters of citric acid, and polyethylene glycols.

As the amount of polymer (A) is increased in relation to that of polymer (B), the rate of release of the active ingredient enclosed in the coated dosage form increases above the pH value at which permeability to the active ingredient sets in. While with low polymer (A) contents the coating membrane becomes permeable but remains intact, with higher polymer (A) levels it disintegrates soon after the pH value at which it becomes permeable is reached, especially when the coated core develops a shattering action by swelling.

As a rule, the polymers (A) and (B) will represent from 10 to 40 weight percent of the aqueous coating composition. The rest will be water, emulsifiers dissolved therein, and optional additives.

In addition to the polymers (A) and (B), the coating composition may contain commonly used dissolved or suspended auxiliary substances and additives. Apart from the film forming aids mentioned, possible additives are preservatives, thickeners, lustering agents, dyes and pigments, for example.

The viscosity of the liquid coating composition advantageously ranges from 10 to 100 centipoises. Its pH value should be below 6 and usually is between 2 and 5. The size of the latex particles therein is not critical and the sizes are in the usual range from 0.01 to 1 micron.

All pharmaceutical dosage forms which must be resistant to gastric juice and which must release the enclosed active ingredient in the intestinal tract at a predetermined pH value relatively quickly can be coated in accordance with the invention. As a rule, at least 80 percent of the active ingredient is released within 60 minutes.

Tablets, dragée cores, pills, granules, crystals and powders, and even gelatin capsules can be coated. Granules or pellets can also be manufactured by conventional granulating methods using the compositions of the invention. The granules in turn may be coated or compacted into tablets.

The coating methods correspond to those used with conventional dispersions for coating pharmaceutical dosage forms. Pan coating methods in which the coating is poured or sprayed onto the rotating dosage forms either in portions or continuously are preferred. Usually warm air is then blown onto them to dry them. Fluidized bed coating is also advantageous and is preferably carried out at an air temperature between 40° C. and 60° C.

Although the coating thickness may be as much as 50 microns, the pH-dependent release characteristics are especially apparent with coating thicknesses between 10 and 30 microns. This corresponds to a coating weight between 10 and 20 weight percent, based on the weight of the coated core, in the coating of granules, particles, and crystals, and between 3 and 5 weight percent in the case of tablets, dragees, or capsules. Below this range release is likely to be increasingly time-dependent rather than pH-dependent, and above this range, an increasingly delayed release at the pH value of the dissolution range can be expected.

A better understanding of the present invention and of its many advantages will be had by referring to the following specific examples given by way of illustration.

EXAMPLE 1

141 g of a 30 percent dispersion of a copolymer of equal parts of methacrylic acid and ethyl acrylate (42 g of solids) were mixed with 328 g of a 30 percent dispersion of film forming copolymer of ethyl acrylate and methyl methacrylate in a ratio of 2:1 (98 g of solids). A suspension of 70 g of talc in 514 g of water was then added. The mixture had a pH of 5.7. (The film forming copolymer has a $T_{\lambda max}$ of 29° C. The minimum film forming temperature of the aqueous dispersion is 8° C.).

3 kg of quinine sulfate tablets (each weighing 206.5 mg and having a diameter of 8 mm and a height of 3.7 mm) were preheated to about 32° C. in a coating pan with a diameter of 35 cm rotating at 40 rpm by blowing in warm air at 65° C. to 70° C. and were then continuously sprayed with the aqueous polymer dispersion while warm air continued to be blown in. An air pressure spray gun having a nozzle diameter of 1.0 mm and a spraying pressure of 0.8 bar was used for this purpose. The polymer emulsion was delivered to the spray gun through a hose pump and the spray rate was thus set at about 9 grams/minute. Total spraying time was 2 hours. The coated tablets were then dried further for 2 hours at 40° C. in a circulating air drying cabinet. The coating was 50 microns thick.

When tested in a USP disintegration tester, the tablets were initially resistant to gastric juice at pH 1.3 for 60 minutes. Neither disintegration nor release of the active ingredient occurred even after another 30 minutes in a buffer solution of pH 5.5. Rapid release of active ingredient first occurred in a buffer solution of pH 6.0 (see curve IV) and all tablets disintegrated within 12 to 16 minutes.

EXAMPLE 2

141 g of a 30 percent dispersion of a copolymer of equal parts of methacrylic acid and methyl methacrylate (42 g of solids) were mixed with 328 g of a 30 percent dispersion of a copolymer of ethyl acrylate and methyl methacrylate in the ratio of 2:1 (98 g of solids). A suspension of 70 g of talc in 514 g of water was then added. The pH value was 6.0

3 kg of quinine sulfate tablets were then coated as in Example 1. The coating was 50 microns thick.

When the coated tablets were tested in the USP disintegration tester, they, too, were found to be resistant to gastric juice for 60 minutes. Even after another 30 minutes in a test solution of pH 5.5 and a further 30 minutes in a test solution of pH 6.0, there was no disintegration and no release of active ingredient. Only when a buffer solution of pH 6.5 was then introduced did the tablets disintegrate, within 2 to 11 minutes and with fast release of active ingredient. (See curve V.)

EXAMPLE 3

141 g of a 30 percent dispersion of a copolymer of methacrylic acid and methyl methacrylate in a ratio of 1:2 (42 g of solids) were mixed with 328 g of a 30 percent dispersion of a copolymer of ethyl acrylate and methyl methacrylate in a ratio of 2:1 (98 g of solids). A suspension of 70 g of talc in 514 g of water was then added. The pH value was 6.6.

3 kg of quinine sulfate tablets were coated as in Example 1. The coating was 50 microns thick.

In the USP disintegration tester, the coated tablets were resistant to gastric juice for 60 minutes, and neither disintegration nor appreciable release of active ingredient was observed when they were stirred in test solutions at pH 5.5., 6.0, 6.5 and 7.0, respectively, for 30 minutes each. Only at pH 7.5 did the tablets disintegrate, within 11 to 16 minutes and with rapid release of active ingredient. (Curve VII.)

EXAMPLE 4

1000 g of a 30 percent emulsion polymer of ethyl acrylate and methyl methacrylate in a ratio of 2:1 (300 g of solids) were mixed with a solution of 10 g of polyoxyethylene sorbitan monooleate ("Tween 80") in 20 g of water. To this there were added 1000 g of 30 percent emulsion polymer of equal parts of methacrylic acid and ethyl acrylate (300 g of solids), and then a suspension of 151 g of talc in 582 g water, 1 g of a silicone defoaming emulsion being further admixed. The mixture had a pH of 5.6.

1 kg of theophylline granules of a particle size ranging from 0.3 to 0.8 mm were suspended in a stream of warm air in a fluidized bed apparatus, preheated to about 40° C., and sprayed through a nozzle projecting into the fluidized bed while a stream of hot air of 40° C. was maintained. The nozzle aperture was 1.2 mm; the spraying pressure was 1.8 bars. The spray rate, which was regulated through a hose pump, was 11 grams/minute: the total spraying time was 131 minutes. The total amount of coating applied corresponded to an increase in 20 percent in the weight of the granules and was 25 microns thick. Samples were taken also after 10 and 15 percent of the coating had been applied (respective coating thicknesses of 9 and 19 microns). A significant delay in the dissolution of the active ingredient in the gastric juice was observable even after just 10 percent of the coating had been applied.

The granules coated with 15 percent of the coating mixture were found to be resistant to gastric juice for 120 minutes in the USP paddle apparatus, that is to say the release of active ingredient was less than 5 percent. Rapid release of active ingredient then set in already at pH 5.5.

The granules coated with 20 percent of the coating mixture also proved resistant to gastric juice. At pH 5.5., an initially slow release of active ingredient was observable which sharply increased at pH 6.5.

EXAMPLE 5

1000 g of a 30 percent emulsion polymer of ethyl acrylate and methyl methacrylate in a ratio of 2:1 (300 g of solids) were mixed, after the addition of 10 g of polyoxyethylene sorbitan monooleate in 20 g of water, with 100 g of a 30 percent emulsion polymer of equal parts methacrylic acid and ethyl acrylate (30 g of solids). A spray formulation was prepared from 685 g of this mixture with a suspension of 150 g of talc in 600 g of water. When the constitutents were stirred together, 1 g of a silicone defoaming emulsion was added to suppress foaming. The suspension had a pH of 6.8.

This spray formulation was sprayed onto 1 kg of theophylline granules as described in Example 4. With an application of 5 to 15 percent, the release curves show an approximately linear release of active ingredient in the pH region above 5.5.

What is claimed is:

1. An aqueous dispersion adaptable to use for coating pharmaceutical dosage forms, said dispersion having a pH below 6 and comprising
    (A) dispersed latex particles of a polymer containing carboxyl groups which is water insoluble at a pH below 5 but becomes water soluble at least in a portion of the pH range between pH 5 and pH 8, and (B) dispersed latex particles of a water insoluble film forming polymer.

2. An aqueous dispersion as in claim 1 wherein said polymers (A) and (B) are emulsion polymers of vinyl and/or vinylidene monomers.

3. An aqueous dispersion as in claim 2 wherein said polymer containing carboxyl groups contains from 10 to 70 weight percent of at least one of acrylic acid and methacrylic acid.

4. An aqueous dispersion as in claim 2 wherein said polymers (A) and (B) comprise alkyl esters of acrylic acid and/or methacrylic acid.

5. An aqueous dispersion as in claim 2 having a combined content of said polymers (A) and (B) from 10 to 40 percent by weight.

6. An aqueous dispersion as in claim 1 wherein said film forming polymer has a dynamic glass transition temperature between 10° C. and 60° C.

7. A method for making a coated pharmaceutical dosage form resistant to gastric juice which comprises coating a medicament core with an aqueous dispersion of a coating composition as in claim 1 and drying said coated core.

8. A method as in claim 7 wherein the coated pharmaceutical dosage form is dried with air at a temperature below 60° C.

9. A pharmaceutical dosage form resistant to gastric juice comprising a medicament core having thereover a coating comprising (A) a polymer containing carboxyl groups which is water insoluble at a pH below 5 but becomes water soluble at least in a portion of the pH range between pH 5 and pH 8, and (B) a water insoluble film forming polymer, in a weight ratio between 60:40 and 5:95.

10. A pharmaceutical dosage form as in claim 9 wherein said coating has a thickness between 10 and 50 microns.

11. A pharmaceutical dosage form as in claim 9 in the form of small particles wherein the weight of said coating is between 10 and 20 percent by weight of the coated core.

12. A pharmaceutical dosage form as in claim 9 in the form of tablets, dragées, or capsules wherein the weight of said coating is between 3 and 5 percent by weight of the coated core.

* * * * *